United States Patent [19]
Hadley et al.

[11] Patent Number: 5,683,981
[45] Date of Patent: Nov. 4, 1997

[54] CYCLIC BRIDGED ANALOGS OF α-MSH AND METHODS THEREOF

[75] Inventors: Mac E. Hadley; Victor J. Hruby, both of Tucson, Ariz.; Shubh D. Sharma, Albuquerque, N. Mex.

[73] Assignee: Competitive Technologies, Inc., Fairfield, Conn.

[21] Appl. No.: 470,343

[22] Filed: Jun. 6, 1995

Related U.S. Application Data

[63] Continuation-in-part of Ser. No. 199,775, Feb. 22, 1994, abandoned, which is a continuation of Ser. No. 938,781, Aug. 31, 1992, abandoned, which is a continuation-in-part of Ser. No. 611,456, Nov. 13, 1990, abandoned, which is a continuation of Ser. No. 212,807, Jun. 29, 1988, abandoned, which is a continuation-in-part of Ser. No. 53,229, May 22, 1987, abandoned.

[51] Int. Cl.[6] .......................... A61K 38/00; A61K 38/02; C07K 5/00; C07K 7/00
[52] U.S. Cl. .......................... 514/11; 530/317; 530/312
[58] Field of Search .................. 514/11; 530/312, 530/317

[56] References Cited

FOREIGN PATENT DOCUMENTS 0292291  11/1988   European Pat. Off. .......... C07K 7/00

OTHER PUBLICATIONS

Victor J. Hruby, *Life Science*, vol. 31, pp. 189–199 No. 3, 1982.

Al–Obeidi et al, *J. Med. Chem*, vol. 32, pp. 2555–2561, 1989.

*Primary Examiner*—Avis M. Davenport
*Attorney, Agent, or Firm*—Yahwak & Associates

[57] ABSTRACT

A novel class of cyclic bridged analogs of α-MSH are described herein. With the described analogs, when administered in pharmaceutical compositions, it is now possible to achieve normalization of hypopigmentation dysfunctions and to achieve darkening of the skin in the total absence of sun or UV light irradiation.

18 Claims, No Drawings

CYCLIC BRIDGED ANALOGS OF α-MSH AND METHODS THEREOF

This is a continuation-in-part of our earlier filed U.S. patent application Ser. No. of 199,775, filed Feb. 22nd 1994 and now abandoned, which in turn is a continuation of U.S. patent application Ser. No. of 938,781, filed on Aug. 31st 1992 and now abandoned, which in turn is a continuation-in-part of U.S. patent application Ser. No. of 611,456, filed on Nov. 13th 1990 and now abandoned, which in turn is a continuation of U.S. patent application Ser. No. of 212,807, filed on Jun. 29th 1988 and now abandoned which in turn is a continuation-in-part of U.S. patent application of Ser. No. 53,229 filed on May 22nd 1987 and now abandoned.

In view of partial support provided by grants from the United States Public Health Service and the National Science Foundation in the making of the present invention, the United States Government has certain statutory rights to the present invention under 35 USC 200 et seq.

The present invention concerns a class of previously unreported cyclic bridged analogues of α-MSH, the method of stimulating melanocytes in vertebrates by the administration of these analogues, and to the compositions useful in the method.

In vertebrates, the color of their skin, fur, and feathers is determined by the number and distribution of certain color-bearing cells, e.g. melanocytes, the number of which is under genetic control. Melanocytes in mammals are localized at the basal layer of the epidermis, at the dermal-epidermal junction, and within hair follicles. Synthesis of pigment (melanin) within these melanocytes is controlled by the activity of an enzyme, tyrosinase, which is localized in an intracellular organelle, the premelanosome. Upon activation of tyrosinase, either eumelanin (brown-black) or phaeomelanin (yellow-red) pigment is deposited within the organelle; after complete melanization, the premelanosome is known as a melanosome, more specifically either an eumelanosome or a phaemelanosome depending upon color [see Jap. J. Derm. 79:278 (1969)]. Melanosomes are delivered to surrounding keratinocytes of the skin or to cells within the shaft of the growing hair by the process known as cytocrine secretion.

Although melanin synthesis and pelage patterns are expressed genetically, follicular melanogenesis and pelage color changes in some mammals may be hormonally controlled by a linear tridecapeptide alpha-melanotropin (also known as alpha-melanocyte stimulating hormone or α-MSH).

Alpha-MSH is derived from a large molecular weight precursor protein, proopiomelanocortin, and is secreted by the pars intermedia of the pituitary gland. The hormone has a wide variety of putative physiological activities including the control of melanin pigmentation of skin, the stimulation of melanocyte adenylate cyclase activity, tyrosinase activity, and subsequent melanin production [see Pigment Cell 6:323 (1980)], a variety of effects on central nervous system activities such as memory, learning and attention. [see Peptides 3:353 (1992), and Synapse 2:288 (1988)]

In humans, α-MSH is apparently found only in the pituitary gland of the fetus and not in the adult. In adult humans, a certain level of melanin production is genetically determined and constitutively present. Variable melanin synthesis above and beyond this baseline level is directly dependent on UVL stimulation, e.g. sunlight; exposure to high levels of sunlight triggers increased production of melanin, with concomitant darkening of the skin. This response may be an evolutionary adaptation to protect the person against the aging and mutagenic properties of UVL. Exposure to low levels of UVL results in lower levels of integumental melanin synthesis, fading of skin color, and a diminished blocking effect allowing the skin to absorb greater amounts of radiation. Although adults do not synthesize α-MSH in the pituitary gland, human melanocytes will respond to this hormone (and a racemized preparation thereof).

Hypopigmentation of the skin in humans results from local defects in melanin production within the melanocytes, however, the etiology for many such hypopigmentary disturbances is still unknown.

It is estimated that approximately 1% of the world's population is afflicted with some form of hypopigmentation dysfunction. Although it is known that α-MSH and certain analogues of α-MSH can cause darkening in amphibians when administered subcutaneously, and that α-MSH is associated with skin darkening in adrenalectomized humans when administered intramuscularly [see, New England Journal of Medicine 270:539 (1964)], these routes of administration are not suitable for repeated application necessary to achieve and maintain the desired effect.

Prior to the research described in our earlier U.S. Pat. Nos. 4,457,864, 4,485,039 4,886,038, 4,918,055 and 5,049, 547, and U.S. patent application Ser. No. 916,767, now abandoned, the disclosures of which are incorporated in toto herein, no adequate means of treating these hypopigmentation disorders were known. As disclosed in these prior descriptions, it has been discovered that certain analogues of α-MSH can effectively be administered in a number of different modes of administration (including topical, transdermal, transcutaneous, oral, intravenous, and other modes of administration) and these analogues will reach the melanocytes in active form to stimulate the production of melanin. From this previous research it was further discovered that the replacement of methionine with norleucine in the active linear core heptapeptide gave a potent analogue of α-MSH. In addition, substitution of phenylalanine at position 7 with its enantiomer D-phenylalanine, resulted in a more biologically potent analogue having prolonged activity in both recognized (frog and lizard skin) bioassays.

In addition to providing teachings of the various modes by which α-MSH and its analogues may be administered, our prior inventions have included a series of novel α-MSH analogues which show superior activity to the naturally occurring hormone. Thus, from the naturally occurring peptide we determined that the substitution of the D-isomer at position 7 to provide similar structures to:

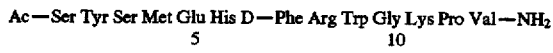

(conventionally written Ac-[D-Phe$^7$]α-MSH$_{1-13}$NH$_2$) greatly improved the activity of the hormone; further investigations showed a new generation of cyclic 4–10 disulfide analogues with structures similar to:

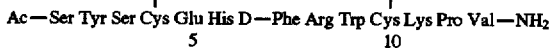

(or as conventionally written

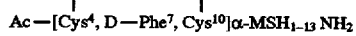

which also had unexpected potency when compared to the naturally occurring hormone; continued investigations showed a second generation of cyclic 5–10 lactam analogues with structures similar to:

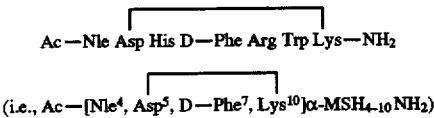

(i.e., Ac—[Nle$^4$, Asp$^5$, D—Phe$^7$, Lys$^{10}$]α-MSH$_{4-10}$NH$_2$)

Continued research has now led to the discovery of a third generation of cyclic 5–10/11 peptide bridged cyclic analogues which are potent stimulants for melanocytes in vertebrates. These new cyclic analogues according to the present invention belong to the class having the general structure:

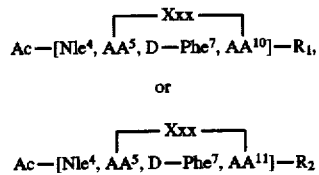

wherein AA$^5$ may be either a L- or D- amino acid having an omega-amino or carboxyl group in the side chain, for example AA$^5$ may be α,γ-diaminopropionic acid, α,γ-diaminobutyric acid, Orn, Lys, α-aminoadipic acid, α-aminopimelic acid, or higher (i.e. alkyldionic acids containing more than 7 carbons) homologs, Glu or Asp; wherein AA$^{10}$ may be either a L- or D- amino acid having an omega-amino or carboxyl group in the side chain, for example, AA$^{10}$ may be diaminopropionic acid, α,γ-diaminobutyric acid, Orn, Lys, α,β-aminoadipic acid, α-aminopimelic acid, or higher homologs, Glu or Asp; wherein R$_1$ is the designation α-MSH$_{1-13}$NH$_2$, α-MSH$_{1-12}$NH$_2$, α-MSH$_{1-11}$NH$_2$, α-MSH$_{4-13}$NH$_2$, or α-MSH$_{4-10}$NH$_2$; wherein AA$^{11}$ may be a L- or D- amino acid having an omega-amino or carboxyl group in the side chain, for example, AA$^{11}$ may be α,β-diaminopropionic acid, α,γ-diaminobutyric acid, Orn, Lys, a-aminoadipic acid, α-aminopimelic acid, or higher homologs, Glu or Asp; wherein R$_2$ is the designation α-MSH$_{1-13}$NH$_2$, α-MSH$_{1-12}$NH$_2$, α-MSH$_{1-11}$NH$_2$, α-MSH$_{4-13}$NH$_2$, or α-MSH$_{4-10}$NH$_2$; and wherein Xxx may be from 1 to 5 a-amino acid residues each of which may be of L- or D- configuration (such as, for example, Lys-Lys, Lys-Arg, Arg-Lys, Arg-Arg, Ser-Ser, or Nle-Nle), or a linear or branched chain spacer of, for example, the type NH$_2$-(CH$_2$)n-COOH, NH$_2$-(CH$_2$)n-NH$_2$, or HOOC-(CH$_2$)n-COOH wherein "n" may be an integer from 1 to 15.

More particularly, a preferred class of analogues according to the present invention are those wherein AA$^5$ is selected from the group of Glu and Asp; wherein AA$^{10}$ is Lys; wherein AA$^{11}$ is Lys; wherein R$_1$ is selected from the group of α-MSH$_{1-13}$ and α-MSH$_{4-10}$; wherein R$_2$ is selected from the group of α-MSH$_{1-13}$, α-MSH$_{4-13}$, and α-MSH$_{4-10}$; and wherein Xxx is selected from the group of Arg-Arg, Arg-Lys, Lys-Arg, Lys-Lys, Nle-Nle, Lys, D-Lys-D-Lys, Glu-Glu, Ser-Ser, and NH(CH$_2$)$_5$CO.

Thus, according to the present invention, it is now possible and convenient to administer compositions comprising the cyclic bridged α-MSH analogues of the present invention to achieve normalization of hypopigmentation dysfunctions such as post inflammatory hypopigmentation, including pityriasis, alba, tinea versicolor, vitiligo, idiopathic guttae hypomelanosis; and nevus depigmentosus. In addition, it is now possible to achieve darkening of the skin in the total absence of sun or UV light irradiation.

A more thorough and complete understanding of the cyclic bridge analogs of alpha melanotropin can be obtained by reference to the following examples which are presented by way of illustration only and are not intended, nor should they be considered, to limit the scope of the claimed invention.

In these following examples, prior treatment of reagents was performed to standardize the examples. All cyclic peptides were synthesized by solid phase peptide synthesis using p-methylbenzhydrylamine resin (Peptides International or Bachem) which was swelled in DCM (dichloromethane) for three hours, neutralized with 10%DIEA/DCM, (DIEA is N,N-diisopropylethylamine) and washed with DCM three times before use. All the amino acids (Bachem or manufactured from protocols within the literature) were of the L-configuration with the exception of phenylalanine which was of the D-configuration.

In the following description, DIC refers to diisopropylcarbodiimide; HOBt refers to hydroxybenzotriazole; TFA refers to trifluoroacetic acid; Bom refers to benzyloxymethyl; NMP refers to 4-methyl-2-pyrolidinone; Fmoc refers to fluorenylmethyloxycarbonyl; For refers to formyl; Tos refers to tosyl; Boc refers to tert-butyloxycarbonyl; Bzl refers to benzyl; OFm refers to fluorenylmethyl ester; and Bop refers to benzotriazolyl N-oxytridimethylaminophosphonium hexafluorophosphate.

EXAMPLE 1

Peptides were synthesized according to well established methods of solid-phase methods of peptide synthesis [See J. M. Stewart and G. T. Young, Solid Phase Peptide Synthesis, Pierce Chemical Company, Rockford, Ill. (1984), and J. Medicinal Chemistry 32:2555–2561 (1989)] using p-methylbenzhydrylamine resin (pMBHA resin, substitution 0.35 meq/gm) as a solid support. Successively, individual amino acid derivatives N$^α$-Boc-Val, N$^α$-Boc-Pro, N$^α$-Boc-Lys(N$^ε$-Fmoc), N$^α$-Boc-Gly, N$^α$-Boc-Trp, N$^α$-Boc-Arg(N$^g$-Tos), N$^α$-Boc-D-Phe, and N$^α$-Boc-His(N$^{im}$-Bom) were coupled to the resin using diisopropylcarbodiimide-N-hydroxybenzotriazole as a coupling reagent and trifluoroacetic acid-anisole-dichloromethane, [48:2:50 (v:v:v)], as a N$^α$-Boc deblocking reagent. The peptide resin, Boc-His(Bom)-D-Phe-Arg(Tos)-Trp-Gly-Lys(Fmoc)-Pro-Val-Resin, was treated with 20% piperidine in N-methyl-2-pyrolidinone for 20 min. to remove the N$^ε$-Fmoc group on the lysine residue. The resulting peptide-resin, with a free side chain amino function in the lysine residue, was termed "key intermediate A".

N$^α$-Fmoc-Lys(N$^ε$-ClZ) was coupled to this amino function by the DIC-HOBt method. After the removal of the N$^α$-Fmoc group by treatment with 20% piperidine in NMP, N$^α$-Fmoc-Arg(N$^g$-Tos) was coupled by similar method. This was followed by the removal of the N$^α$-Boc group from the histidine residue by the treatment of the peptide-resin with TFA-anisole-DCM mixture as described above. N$^α$-Boc-Glu (γ-OFm) was then coupled to the growing peptide by DIC-HOBt method. The Fmoc and OFm groups were simultaneously removed by the treatment of the peptide-resin with 20% piperidine in NMP, and the two newly freed groups, α-NH$_2$ of Arg and γ-COOH of Glu respectively, were condensed using benzotriazolyl N-oxytridimethylaminophosphonium hexafluorophosphate reagent to establish a cyclic structure. After removal of the N$^α$-Boc group from the Glu residue, the couplings of successive amino acids, viz N$^α$-Boc-Nle, N$^α$-Boc-Ser(Bzl), N$^α$-Boc-Tyr(Cl$_2$Bzl), and N$^α$-Boc-Ser(Bzl) were accomplished using the DIC-HOBt method. Finally, the deblocking of the N-terminal Boc group, and acetylation of the resulting amino function, resulted in a fully protected peptide resin. This was dried and treated with HF in the presence of anisole to deprotect the protecting groups on the amino acid side chains and release the peptide from the resin. The crude peptide, SHU-9014, thus obtained was purified by reversed phase high performance liquid chromatography (RP-HPLC).

Alternatively, after the coupling of $N^\alpha$-Boc-Glu($\gamma$-OFm) to the peptide resin as described above, the synthesis was continued further by deblocking the Boc group and coupling the successive amino acids, viz. $N^\alpha$-Boc-Nle, $N^\alpha$-Boc-Ser (Bzl), $N^\alpha$-Boc-Tyr(Cl$_2$Bzl) and $N^\alpha$-Boc-Ser(Bzl). The ultimate N-terminal Boc group was deblocked and the free amino function acetylated. The $N^\alpha$-Fmoc and $\gamma$-OFm functionalities from the Arg and Glu residues were then removed by treatment with 20% piperidine in NMP and the resulting two functionalities condensed using the BOP reagent to establish the cyclized bridge formation. Further treatments, such as reaction with HF and purification of the resulting crude peptide by HPLC were performed as described before.

EXAMPLE 2

A portion of the key intermediate A, as obtained in Example 1, was treated similarly with $N^\alpha$-Fmoc-Lys($N^\epsilon$-ZCl) in the presence of DIC-HOBt as described earlier to couple this amino acid derivative. After the removal of the Fmoc group as described in Example 1, $N^\alpha$-Fmoc-Lys($N^\epsilon$-ClZ), instead of $N^\alpha$-Fmoc-Arg($N^g$-Tos), was coupled to the peptide-resin in a similar fashion. Further synthetic protocols were followed as described in Example 1. This procedure resulted in the synthesis of peptide SHU-9009.

EXAMPLE 3

A second portion of the key intermediate A, as described in Example 1, was treated with $N^\alpha$-Fmoc-Arg($N^g$-Tos), instead of $N^\alpha$-Fmoc-Lys(ClZ), using similar DIC-HOBt methodology. This was followed by further treatments as described in Example 1. This procedure resulted in the synthesis of the peptide SHU-9002.

EXAMPLE 4

Similar to the successive treatment of the key intermediate A with $N^\alpha$-Fmoc-Lys($N^\epsilon$-ZCl) and $N^\alpha$-Fmoc-Arg($N^g$-Tos) as described in the Example 1, a third portion of this key intermediate was treated with $N^\alpha$-Fmoc-Arg($N^g$-Tos) and $N^\alpha$-Fmoc-Lys($N^\epsilon$-ZCl). Prior protocols described above were followed thereafter to obtain the cyclic bridged peptide SHU-9010.

EXAMPLE 5

To a 0.5 mmole sample of the pMBHA resin (substitution 0.35 meg/gm) the following amino acids were successively coupled using the DIC-HOBt procedure as described in Example 1: $N^\alpha$-Boc-Lys($N^\epsilon$-Fmoc), $N^\alpha$-Boc-Trp, $N^\alpha$-Boc-Arg($N^g$-Tos), $N^\alpha$-Boc-D-Phe, and $N^\alpha$-Boc-His($N^\pi$-Bom). The resin-peptide was then treated with 20% piperidine in NMP for 20 min. to remove the $N^\epsilon$-Fmoc group from the Lys amino acid residue. The resulting peptide-resin, $N^\alpha$-Boc-His(Bom)-D-Phe-Arg(Tos)-Trp-Lys-Resin, having a free NH$_2$ group in the side chain of the Lys amino acid residue, was termed "key intermediate B".

$N^\alpha$-Fmoc-Lys($N^\epsilon$-ClZ) was coupled to this amino function by DIC-HOBt method. After the removal of the $N^\alpha$-Fmoc group by treatment with 20% piperidine in NMP, $N^\alpha$-Fmoc-Arg($N^g$-Tos) was coupled by a similar method. This was followed by the removal of the $N^\alpha$-Boc group from the histidine residue by the treatment of the peptide-resin with TFA-anisole-DCM mixture as described earlier. $N^\alpha$-Boc-Asp($\beta$-OFm) was then coupled to the resin-peptide by the DIC-HOBt method. The Fmoc and OFm groups were simultaneously removed by the treatment of the peptide-resin with 20% piperidine in NMP, and the two newly freed groups, $\alpha$-NH$_2$ of Arg and $\gamma$-COOH of Asp respectively, were condensed using the BOP reagent to establish a cyclic structure. After removal of the $N^\alpha$-Boc group from the Asp amino acid residue, the coupling of $N^\alpha$-Boc-Nle was accomplished by the DIC-HOBt method. The $N^\alpha$-Boc group was deblocked, and the generated amino group was acetylated to afford the fully protected peptide resin. This was dried and treated with HF in the presence of anisole to deprotect the protecting groups on the amino acid side chains and to release the peptide from the resin. The crude peptide, SHU-9021, thus obtained, was purified by reversed phase high performance liquid chromatography.

Alternatively, after the coupling of $N^\alpha$-Boc-Asp($\beta$-OFm) to the peptide resin, as described above, the synthesis was continued further by deblocking the Boc group and coupling $N^\alpha$-Boc-Nle by the DIC-HOBt method. The N-terminal Boc group was deblocked and the free amino function acetylated. The $N^\alpha$-Fmoc and $\gamma$-OFm functionalities from the Arg and Asp amino acid residues were removed by treatment with 20% piperidine in NMP and the resulting two functionalities condensed using the BOP reagent to establish the cyclic bridge. Further treatments, such as reaction with HF and purification of the resulting crude peptide by RP-HPLC were performed as described above.

EXAMPLE 6

A portion of key intermediate B, as obtained in Example 5, was treated with $N^\alpha$-Fmoc-Lys($N^\epsilon$-ClZ) in the presence of DIC-HOBt as described earlier to couple this amino acid to the resin. After the removal of the Fmoc group as described in Example 5, $N^\alpha$-Fmoc-Lys($N^\epsilon$-ClZ), instead of $N^\alpha$-Fmoc-Arg($N^g$-Tos), was coupled to the peptide-resin in a similar fashion. Further synthetic protocols were followed to those described in Example 5. This procedure resulted in the synthesis of peptide SHU-9019.

EXAMPLE 7

A second portion of key intermediate B was treated with $N^\alpha$-Fmoc-Arg($N^g$-Tos), instead of $N^\alpha$-Fmoc-Lys(ClZ), using a similar DIC-HOBt procedure. This was followed by the appropriate treatments, as described in the Example 5, to obtain the peptide SHU-9020.

EXAMPLE 8

Similar to the successive treatment of key intermediate B with $N^\alpha$-Fmoc-Lys($N^\epsilon$-ClZ) and $N^\alpha$-Fmoc-Arg($N^g$-Tos) as described in the Example 5, another portion of this key intermediate was treated with $N^\alpha$-Fmoc-Arg($N^g$-Tos) and $N^\alpha$-Fmoc-Lys($N^\epsilon$-ClZ). Further synthetic protocols were followed to those described in Example 5 to obtain the synthesis of the cyclic bridged peptide SHU-9018.

EXAMPLE 9

The peptides described above were examined to determine the relative potencies of the peptides in respect to the stimulation of a melanosome dispersion in vitro using the frog (*Rana pipiens*) and the lizard (*Anolis carolinensis*) [see Science 213:1025 (1981)]. These assays are recognized by the scientific communitty to be a fairly accurate representation of results that would be expected when the test substances are administered to vertebrates in vivo; if activity is found when the test substances are tested in the frog skin assay and the lizard skin assay, similar activity would be expected if the test substances are administered to vertebrates, i.e. darkening in the two assays would indicate that darkening would also occur in vertebrates. These assays measure the amount of light reflected from the surface of the skins in vitro. In response to melanotropic peptides, melanosomes within integumental melanocytes migrate from a perinuclear position into the dendritic processes of the pigment cells. This centrifugal organellar dispersion results in a change of color (darkening) of the skins which is measured by a Photovolt reflectometer and is expressed as the percent response compared to the initial (time zero) reflectance value.

The peptides SHU-9002, 9009, 9010 and 9014 according to the present invention were either more potent or as potent as [$Nle^4$, $D-Phe^7$]-α-MSH [U.S. Pat. No. 4,457,864]. Similarly, the peptides SHU-9018, 9019, 9020 and 9021, were similar in their potency as Ac-Nle-[$Asp^5$-$D-Phe^7$, $Lys^{10}$]. α-$MSH_{4-10}$-$NH_2$ [see J. Medicinal Chem., 32:2555 (1989)].

An interesting feature of some of these peptides, e.g., SHU-9002 and 9010, was that they exhibited creeping potency in the frog skin bioassay, i.e. the percentage skin darkening exhibited by these peptides at a particular dose increased as a function of time. Similar observations have been reported for certain other classes of melanotropic peptides [see J. Medicinal Chem., 35:118 (1992)].

The results of these assays appear in the following table:

TABLE I

Comparative Biological Activities Of Cyclic Bridged Analogs Of Alpha-Melanotropin

| Peptide Assay | Structure | Potencies Relative to α-MSH[a] | |
|---|---|---|---|
| | | Frog Skin Assay | Lizard Skin |
| | alpha-melanotropin | 1 (−)[b] | 1 (−) |
| SHU 9027 | Ac−[$Lys^{3,4}$, D−$Phe^7$]-α-$MSH_{1-13}$−$NH_2$ | 0.4 (−) | NA[c] |
| SHU 9002 | ⌐Arg−Arg⌐<br>Ac−[$Nle^4$, $Glu^5$, D−$Phe^7$, $Lys^{11}$]-α-$MSH_{1-13}$−$NH_2$ | 25 (+) | 2 (+) |
| SHU 9014 | ⌐Arg−Lys⌐<br>Ac−[$Nle^4$, $Glu^5$, D−$Phe^7$, $Lys^{11}$]-α-$MSH_{1-13}$−$NH_2$ | 20 (+) | 4 (+) |
| SHU 9010 | ⌐Lys−Arg⌐<br>Ac−[$Nle^4$, $Glu^5$, D−$Phe^7$, $Lys^{11}$]-α-$MSH_{1-13}$−$NH_2$ | 145 (+) | NA[c] |
| SHU 9009 | ⌐Lys−Lys⌐<br>Ac−[$Nle^4$, $Glu^5$, D−$Phe^7$, $Lys^{11}$]-α-$MSH_{1-13}$−$NH_2$ | 100 (+) | 5 (+) |
| SHU 9013 | ⌐Arg−Lys⌐<br>Ac−[$Lys^{3,4}$, $Glu^5$, D−$Phe^7$, $Lys^{11}$]-α-$MSH_{1-13}$−$NH_2$ | 1 (+) | 4 (+) |
| SHU 9026 | ⌐Nle−Nle⌐<br>Ac−[$Nle^4$, $Glu^5$, D−$Phe^7$, $Lys^{11}$]-α-$MSH_{1-13}$−$NH_2$ | 7 (+) | NA[c] |
| SHU 9020 | ⌐Arg−Arg⌐<br>Ac−[$Nle^4$, $Asp^5$, D−$Phe^7$, $Lys^{10}$]-α-$MSH_{4-10}$−$NH_2$ | 0.14 (−) | 6.7 (+) |
| SHU 9021 | ⌐Arg−Lys⌐<br>Ac−[$Nle^4$, $Asp^5$, D−$Phe^7$, $Lys^{10}$]-α-$MSH_{4-10}$−$NH_2$ | 0.25 (−) | 13.4 (+) |
| SHU 9018 | ⌐Lys−Arg⌐<br>Ac−[$Nle^4$, $Asp^5$, D−$Phe^7$, $Lys^{10}$]-α-$MSH_{4-10}$−$NH_2$ | 0.05 (−) | 10 (+) |
| SHU 9019 | ⌐Lys−Lys⌐<br>Ac−[$Nle^4$, $Glu^5$, D−$Phe^7$, $Lys^{10}$]-α-$MSH_{4-10}$−$NH_2$ | NAc | 12.5 (+) |
| SHU-9205 | ⌐         ⌐<br>Ac−[$Nle^4$, $Glu^5$, D−$Phe^7$, $Lys^{11}$]-α-$MSH_{1-13}$−$NH_2$ | 1.3 (+) | NA[c] |
| | ⌐−−Lys−−⌐<br>Ac−[$Nle^4$, $Glu^5$, D−$Phe^7$, $Lys^{11}$]-α-$MSH_{1-13}$−$NH_2$ | NAc | NA[c] |
| SHU-9210 | ⌐D-Lys−D-Lys⌐<br>Ac−[$Nle^4$, $Glu^5$, D−−−−−$Phe^7$, $Lys^{11}$]-α-$MSH_{1-13}$−$NH_2$ | 3.5 (+) | NA[c] |

TABLE I-continued
Comparative Biological Activities Of Cyclic Bridged Analogs Of Alpha-Melanotropin

| Peptide Assay | Structure | Potencies Relative to α-MSH[a] | |
|---|---|---|---|
| | | Frog Skin Assay | Lizard Skin |
| SHU-9207 | 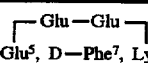 Ac—[Nle⁴, Glu⁵, D—Phe⁷, Lys¹¹]-α-MSH₁₋₁₃—NH₂ with Glu—Glu bridge | 1.3 (+) | NA[c] |
| SHU-9209 | 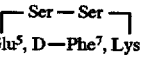 Ac—[Nle⁴, Glu⁵, D—Phe⁷, Lys¹¹]-α-MSH₁₋₁₃—NH₂ with Ser—Ser bridge | 5 (+) | NA[c] |
| | 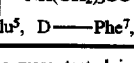 Ac—[Nle⁴, Glu⁵, D——Phe⁷, Lys¹¹]-α-MSH₁₋₁₃—NH₂ with NH(CH₂)₅CO bridge | NA[c] | NA[c] |

[a] = all peptide derivatives were tested in the range of $10^{-12}$ to $10^{-9}$ M concentration; compared to the half-maximal effective dose of a-MSH in the frog skin assay ($10^{-10}$ M), or in the lizard skin assay ($10^{-9}$ M).
[b] = indicates that the response is prolonged (+), or not prolonged (−).
[c] = indicates not assayed.

EXAMPLE 10

0.3 μmole of peptide SHU-9002 was dissolved in 1 ml solution of homogenized crude cell membranes, obtained from about 0.6 million B-16 mouse melanoma cells, in phosphate buffer. After 5 hrs, the suspension was centrifuged at 10,000×g for 10 min. The pellet was saved and the supernatant subjected to HPLC on a C-18 column. This gave no evidence for the presence of the peptide SHU-9002 in the supernatant. A similar procedure repeated with a control peptide,[Nle⁴, D-Phe7]-α-MSH, on the other hand, revealed the presence of this control in the supernatant.

The pellet saved above was treated with DMSO-0.1% aq. TFA mixture (1:1), centrifuged as before and the supernatant subjected to HPLC as earlier. The elution pattern corresponding to the SHU-9002 was obtained. These results showed a marked affinity of the peptide SHU-9002 to the cell membranes.

The significance of the results obtained in Example 10 is that the analogues of the present invention have a higher affinity for the cell membranes than to analogues of α-MSH previously described. Thus, this makes their search for the receptors more facile. The cell membrane has been proposed to act as (i) an "antenna" to capture the peptide hormones, and (ii) to catalyze their subsequent interaction with the receptors [see Proc. Natl. Acad. Sci USA 86:5774 (1986)]. Based upon this concept, the analogues of the present invention, as shown by Example 10, are better "compartmentalized" in the membrane compartment than the aqueous compartment during their interaction with the membrane receptors. This aspect of these analogues according to the present invention make them unique over the prior reported analogues.

In addition to this uniqueness, the analogues of the present invention have other differences when compared with the lactam and disulfide classes of cyclic peptides. The analogues of the present invention are highly amphiphilic (with much better separation of the distinct hydrophilic and hydrophobic phases of the molecule). Increased amphiphilicity is known in establishing a better orientation of the molecule at the receptor site, thereby favorably influencing the biactivity of the molecule [see Ann Rev Biophys. Biophy. Chem 16:561 (1987)].

Another unique property of the present analogues is that the residues at the cyclic bridge part of the molecule have functionally reactive groups, e.g. the ε amino function of the Lys residue. These groups provide the opportunity to further modify the analogues to act as carriers for various reporter groups or other chemical species of therapeutic relevance.

EXAMPLE 11

A sample of key intermediate A, as obtained in Example 1, was treated similarly with $N^\alpha$-Fmoc-D-Lys($N^\epsilon$-ClZ) in the presence of DIC-HOBt as described above to couple this amino acid derivative. After the removal of the Fmoc group as described in Example 1, $N^\alpha$-Fmoc-D-Lys($N^\epsilon$-ClZ), instead of $N^\alpha$-Fmoc-Arg($N^g$-Tos), was again coupled to the peptide in a similar fashion. Further synthetic protocols were similar to that described in Example 1. This resulted in the synthesis of SHU-9210.

EXAMPLE 12

A sample of key intermediate A, as obtained in Example 1, was treated similarly with $N^\alpha$-Fmoc-Ser(BzL) in the presence of DIC-HOBt as described above to couple this amino acid derivative. After the removal of the Fmoc group as described in Example 1, Na-Fmoc-Ser(Bzl) was again coupled to the peptide in a similar fashion. Further synthetic protocols were similar to that described in Example 1. This resulted in the synthesis of SHU-9209.

EXAMPLE 13

Successively, individual amino acid derivatives $N^\alpha$-Boc-Val, $N^\alpha$-Boc-Pro, $N^\alpha$-Fmoc-Lys($N^\epsilon$-Boc), $N^\alpha$-Fmoc-Gly, $N^\alpha$-Fmoc-Trp, $N^\alpha$-Fmoc-Arg($N^g$-Tos), $N^\alpha$-Fmoc-D-Phe, and $N^\alpha$-Fmoc-His($N^\tau$-Bom) were coupled to pMBHA resin (substitution 0.35 meq/gm) using DIC-HOBt as a coupling agent, TFA-anisole-DCM (48:2:50; v/v/v), as $N^\alpha$-Boc and 20% piperidine in NMP as $N^\alpha$-Fmoc deblocking agents. The peptide resin, Fmoc-His(Bom)-D-Phe-Arg(Tos)-Trp-Gly-Lys(Boc)-Pro-Val-Resin, was treated with TFA-anisole-DCM mixture to remove the $N^\epsilon$-Boc group on the lysine residue. To the resulting peptide-resin with a free side chain amino function in the lysine residue $N^\alpha$-Boc-Glu(OBzl) was coupled by the DIC-HOBt method. After removal of the $N^\alpha$-Boc group as above, another similar cycle of coupling $N^\alpha$-Boc-Glu(OBzl) was repeated. This was followed by the removal of the $N^\alpha$-Fmoc group from the histidine residue by the treatment of the peptide-resin with 20% piperidine in NMP as described above. $N^\alpha$-Fmoc-Glu(γ-OBu$^t$) was then coupled to the peptide by the DIC-HOBt method. The Boc and OBu$^t$ groups were simultaneously removed by treatment of the peptide-resin with TFA-anisole-DCM mixture, and the two newly freed groups, α-$NH_2$ of one Glu residue and γ-COOH of the other Glu residue, respectively, were condensed using BOP reagent to establish a cyclic structure. After removal of the $N^α$-Fmoc group from the Glu residue, the couplings of successive amino acids, i.e., $N^α$-Boc-Nle, $N^α$-Boc-Ser(Bzl), $N^α$-Boc-Tyr(BzCL$_2$), and $N^α$-Boc-Ser (Bzl), were accomplished using the DIC-HOBt method. Finally deblocking of the N-terminal Boc group and acetylation of the resulting amino function resulted in a fully protected peptide resin.

This peptide resin was dried and treated with HF in the presence of anisole to deprotect the protecting groups on the amino acid side chains and release the peptide from the resin. The crude peptide, SHU 9207, thus obtained was purified by conventional RP-HPLC techniques.

EXAMPLE 14

A portion of the key intermediate A, obtained from Example 1, was treated with TFA-anisole-DCM mixture to remove the $N^α$-Boc group from the His residue. To the free amino function, thus obtained, $N^α$-Boc-Glu(OFm) was coupled by the DIC-HObt method. The peptide-resin was then treated with 20% piperidine in NMP to deblock both the $N^ε$-Fmoc and γ-OFM function from the Lys and the Glu residues, respectively. The newly liberated NH2 and COOH groups were condensed by using the BOP reagent. After removal of the $N^α$-Boc group from the Glu residue, the couplings of successive amino acids, i.e., $N^α$-Boc-Nle, $N^α$-Boc-Ser(Bzl), $N^α$-Boc-Tyr(BzlCl$_2$), and $N^α$-Boc-Ser (Bzl), were accomplished using the DIC-HOBt method. Finally deblocking of the N-terminal Boc group and acetylation of the resulting amino function resulted in a fully protected resin.

The resin was dried and treated with HF in the presence of anisole to deprotect the protecting groups on the amino acid side chains and release the peptide from the resin. The crude peptide, SHU-9205, thus obtained was purified by conventional RP-HPLC techniques.

EXAMPLE 15

After coupling of $N^α$-Fmoc-Lys($N^ε$-ClZ) to a portion of the key intermediate A, as described in Example 1, the peptide-resin was treated with TFA-anisole-DCM mixture. $N^α$-Boc-Glu(OFm) was then coupled to the peptide as described in Example 1, the peptide analogue having one Lys residue in the cyclic bride part of the molecule was obtained.

EXAMPLE 16

$N^ε$-Fmoc-caproic acid was coupled to a portion of the key intermediate A, as described in Example 1, using DIC-HOBt as the coupling agent. This was then treated with TFA-anisole-DCM mixture. $N^α$-Boc-Glu(OFm) was then coupled to the peptide as described in Example 1. Following similar synthetic protocols described in Example 1, the peptide analogue having a cyclic —NH(CH$_2$)$_5$CO-moiety in the bridge part of the molecule was obtained.

In use for the intended purposes according to the present invention, the compounds according to this invention may be administered transdermally, and by the term "transdermal" is meant any method by which the compounds according to the present invention are introduced across an epidermal layer of cells. For example, transdermal as used in this disclosure encompasses the administration of the compound by topical methods; by intravenous, intramuscular or subcutaneous injection; by solution for use as ocular drops, nasal sprays or tracheal sprays; by the oral route of administration such as by pills, troches, etc.; and by suppositories for vaginal or anal routes of administration. The compound will be formulated in suitable compositions determined by the intended means of administration, according to methods and procedures well-known to those skilled in the art. For example, the compounds suitable for use in this invention may be formulated or compounded into pharmaceutical compositions comprising at least one compound of the present invention (the compositions according to the present invention may comprise one compound or admixtures of compounds according to the present present) in admixture with a solid or liquid pharmaceutical excipient such as a diluent or carrier for enteral or parenteral administration. As injection medium, water containing the usual pharmaceutical additives for injection solutions, such as stabilizing agents, solubilizing agents, and buffers is preferred. Among additives of this type are, for example, tartrate and citrate buffers, ethanol, complex forming agents such as ethylenediamine-tetraacetic acid, and high molecular weight polymers such as liquid polyethylene oxide for viscosity regulation. Solid carrier materials include, for example, starch, lactose, mannitol, methyl cellulose, talc, highly dispersed silicic acid, high molecular weight fatty acids such as stearic acid, gelatine, agar-agar, calcium phosphate, magnesium stearate, animal and vegetable fats, and high molecular weight polymers such as polyethylene glycols. Compositions suitable for oral administration can, if desired, contain flavoring and/or sweetening agents. For topical administration, the compounds may be preferably used with various conventional bases for topical preparations such as creams, ointments, gels, lotions, or sprays, depending upon the desired mode of delivery of the ingredients to an individual. In manufacturing these preparations, the composition may also be mixed with conventional inert excipients such as thickening agents, emollients, surfactants, pigments, perfumes, preservatives, fillers, and emulsifiers, all of which are well known and conventionally used in the formulation of transdermal or other preparations. Typically, these nonactive ingredients will make up the greater part of the final preparation. Preferably, the compositions are manufactured to allow for slow-release or timed-release delivery.

The actual amount of administered compound according to the present invention may vary between fairly wide ranges depending upon the mode of administration, the excipients used, and the degree of stimulation desired. Such amounts are well within the skill of the pharmaceutical scientist to determine, and the amount administered to the mammal being administered to may be any amount chosen to stimulate melanotropic activity.

The remarkable properties of compounds of the invention also render them useful as substitutes for α-MSH and [Nle$^4$]α-MSH in existing diagnostic, therapeutic and basic research schemes. In the area of diagnostic procedures, it is apparent that compounds of the invention, especially those which have been radioiodinated or coupled with gamma radiation emitters, are exceptionally well suited for use in locating and/or differentially characterizing melanoma cells on the basis of association with melanotropin receptors in such cells. The serum stability of compounds of the invention makes them prime candidates in proposed selective drug delivery systems wherein target tissues are known to have high concentrations of melanotropin receptors, and wherein the compounds according to the present invention may be used as a ligand to deliver an anti-cancer or diagnostic molecule (a radioactive label, for example, which can be used to locate melanotropin receptors in the body). The relative high potency and prolonged activity of compounds of the invention in color change-associated phenomena is expected to be duplicated in the context of other biological effects previously noted for naturally occurring melanocyte stimulating hormone and its synthetic analogues.

Thus while we have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Such variations and modifications, for example, would include the substitution of structurally similar amino acid sequences provided herein which function to yield substantially similar melanocyte stimulation to those specifically described above. Thus, changes in sequence by the substitution, deletion, insertion or addition of amino acids (in the peptide sequences) which do not substantially alter the function of those sequences specifically described above are deemed to be within the scope of the present invention. Accordingly, such changes and alterations are properly intended to be within the full range of equivalents, and therefore within the purview of the following claims.

Having thus described our invention and the manner and a process of making and using it in such full, clear, concise and exact terms so as to enable any person skilled in the art to which it pertains, or with which it is most nearly connected, to make and use the same;

We claim:

1. A method of stimulating melanocytes in vertebrates to cause the darkening of said vertebrate's skin coloration without the need to expose said skin to sunlight or UV light irradiation which comprises administering to said vertebrate at least one cyclic analogue of α-MSH selected from the group consisting of:

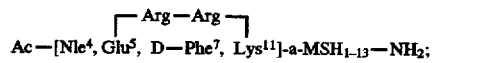
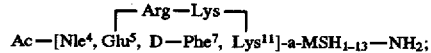
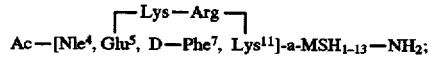
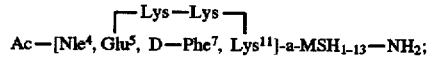
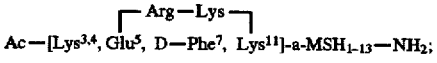
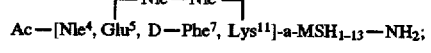
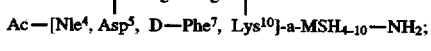
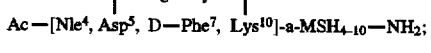
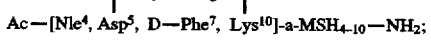
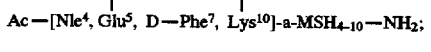
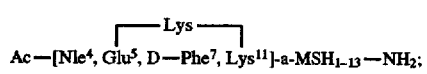
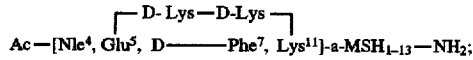
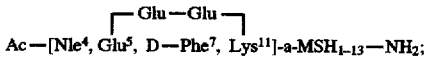
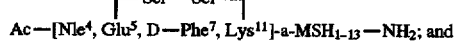
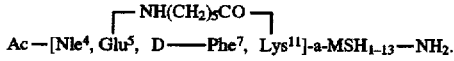

2. A cyclic analogue of alpha-MSH selected from the group consisting of:

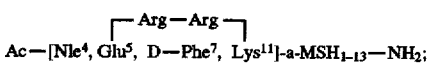
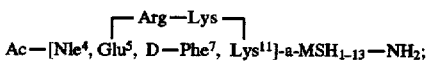
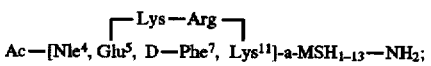
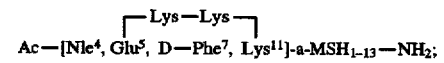
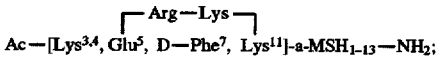
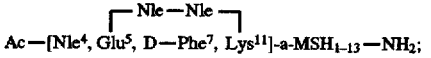
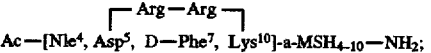
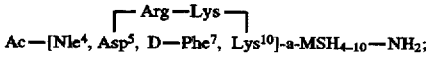
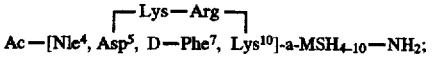
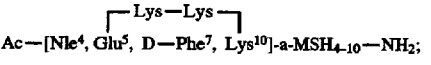
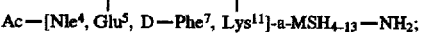
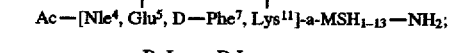
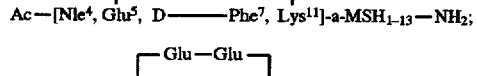
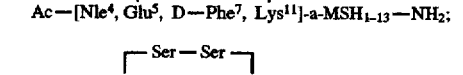
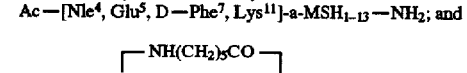

3. An analogue according to claim 2 which is:

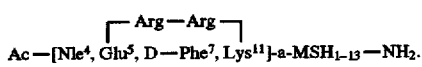

4. An analogue according to claim 2 which is:

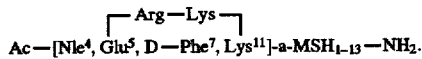

5. An analogue according to claim 2 which is:

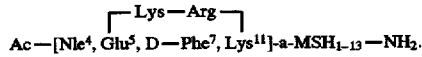

6. An analogue according to claim 2 which is:

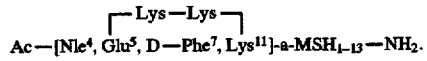

7. An analogue according to claim 2 which is:

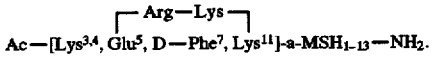

8. An analogue according to claim 2 which is:

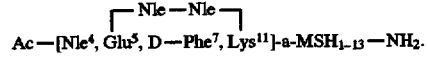

9. An analogue according to claim 2 which is:

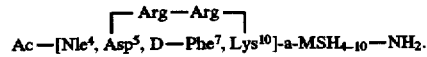

10. An analogue according to claim 2 which is:

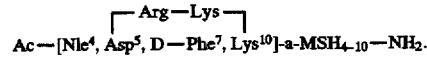

11. An analogue according to claim 2 which is:

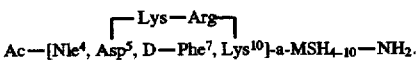

12. An analogue according to claim 2 which is:

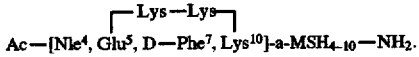

13. An analogue according to claim 2 which is:

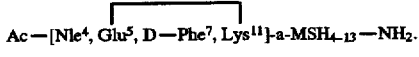

14. An analogue according to claim 2 which is:

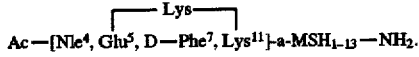

15. An analogue according to claim 2 which is:

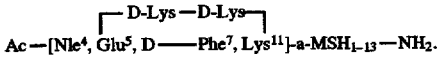

16. An analogue according to claim 2 which is:

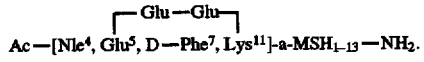

17. An analogue according to claim 2 which is:

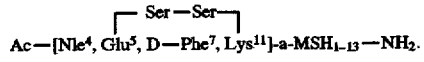

18. An analogue according to claim 2 which is:

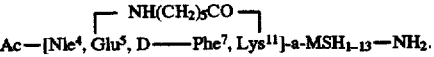

* * * * *